United States Patent
Alshatwi et al.

(10) Patent No.: US 10,682,304 B1
(45) Date of Patent: Jun. 16, 2020

(54) LIGNIN-ZINC OXIDE NANOHYBRID EMULSION FOR UV PROTECTION

(71) Applicant: KING SAUD UNIVERSITY, Riyadh (SA)

(72) Inventors: Ali Abdullah Alshatwi, Riyadh (SA); Jegan Athinarayanan, Riyadh (SA); Vaiyapuri Subbarayan Periasamy, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/697,102

(22) Filed: Nov. 26, 2019

(51) Int. Cl.
*A61K 8/86* (2006.01)
*A61K 8/27* (2006.01)
*A61Q 17/04* (2006.01)
*A61K 8/92* (2006.01)
*A61K 8/06* (2006.01)

(52) U.S. Cl.
CPC .................. *A61K 8/86* (2013.01); *A61K 8/06* (2013.01); *A61K 8/27* (2013.01); *A61K 8/922* (2013.01); *A61Q 17/04* (2013.01)

(58) Field of Classification Search
None
See application file for complete search history.

(56) References Cited

U.S. PATENT DOCUMENTS 9,896,342 B1 2/2018 Alshatwi et al.

FOREIGN PATENT DOCUMENTS

| DE | 2459226 A1 | 6/1976 |
|---|---|---|
| RO | 126904 A2 | 12/2011 |

OTHER PUBLICATIONS

Qian et al., "Sunscreen performance of lignin from different technical resources and their general synergistic effect with synthetic sunscreens", ACS Sustainable Chemistry Engineering (2016), vol. 4, Iss. 7, pp. 4029-4035.
"Sun Protect Date palm" (2017), naolys.com, 4 pages.
Wang et al., "A Novel Lignin/ZnO Hybrid Nanocomposite with Excellent UV-Absorption Ability and Its Application in Transparent Polyurethane Coating", ACS Industrial & Engineering Chemistry Research (2017), vol. 56, pp. 11133-11141.

*Primary Examiner* — Nannette Holloman
(74) *Attorney, Agent, or Firm* — Richard C. Litman; Nath, Goldberg & Meyer

(57) ABSTRACT

A lignin-zinc oxide nanohybrid may be formed by sonication of isolated lignin derived from *Phoenix dactylifera* biomass in an aqueous solution of a soluble zinc salt. The lignin-zinc oxide nanohybrid emulsion or nanoemulsion may then be formed by mixing the lignin-zinc oxide nanohybrid with oil and a stabilizing surfactant and sonicating. The lignin-zinc oxide nanohybrid emulsion effectively bocks UV radiation across the UV spectrum and might therefore be used for UV protection as a sunscreen.

8 Claims, 5 Drawing Sheets

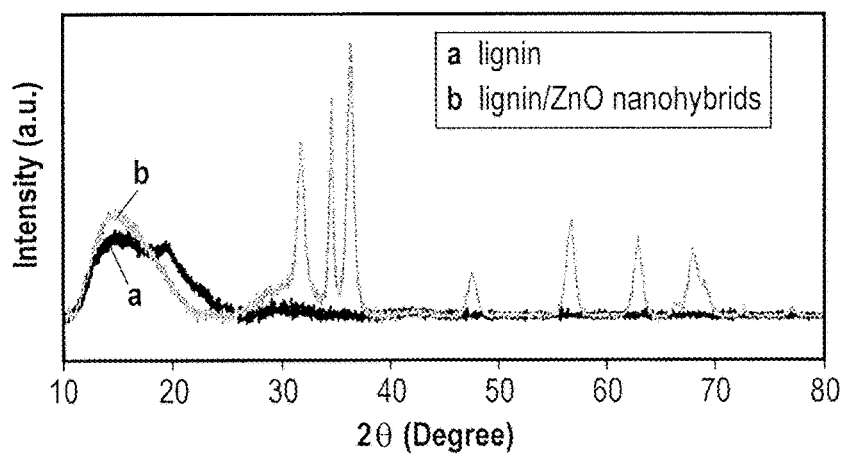
FIG. 2
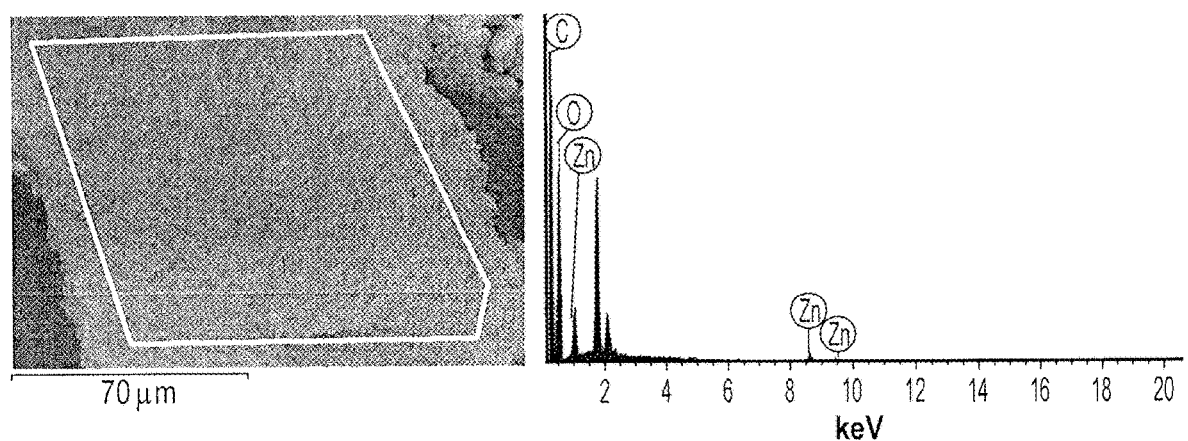
FIG. 3A     FIG. 3B

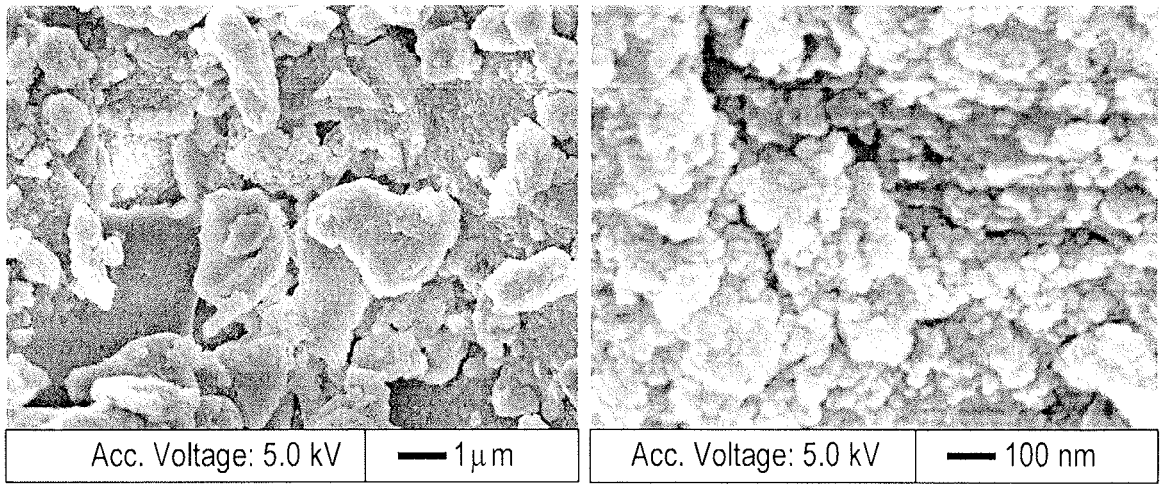
FIG. 5A   FIG. 5B
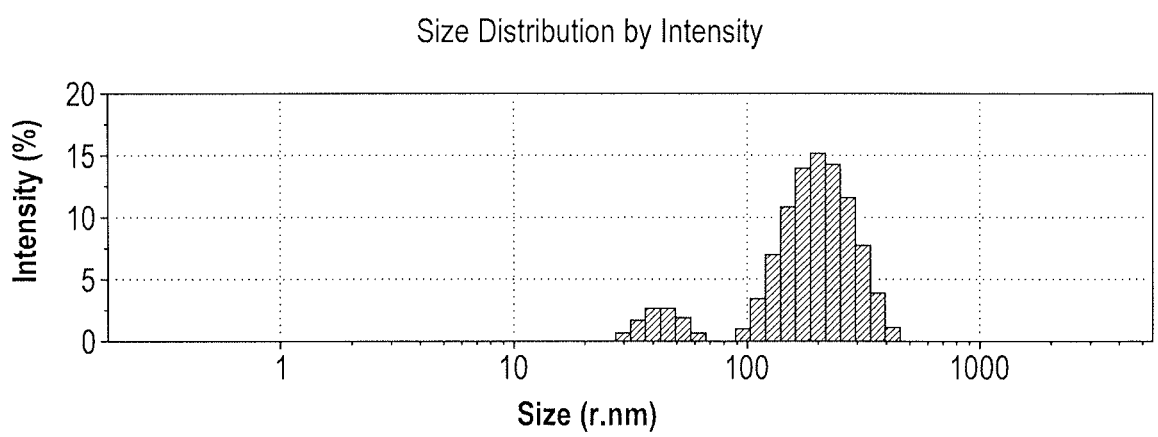
FIG. 6

LIGNIN-ZINC OXIDE NANOHYBRID EMULSION FOR UV PROTECTION

BACKGROUND

1. Field

The disclosure of the present patent application relates to UV protection, and more particularly, to a lignin-zinc oxide nanohybrid emulsion for UV protection.

2. Description of the Related Art

Exposure to ultra violet (UV) radiation (i.e., radiation with wavelengths between 100-400 nm) leads to health risks and injury, such as cataracts, photoconjunctivitis, early skin aging, inflammation in the dermis, other skin problems, and carcinogenesis. UV radiation may be subdivided by wavelength into UVC (200-290 nm), UVB (290-320 nm) and UVA (320-400 nm). Sunscreens available in the market can protect from hazardous UV radiation. Generally, sunscreens are divided into two categories that are based on their mechanism of protection, viz., physical or chemical. However, long-term usage of commercially available synthetic chemical-based sunscreen can cause adverse health and environmental effects. Naturally available plant materials including *Carica papaya* extract, *Rosa kordesii* extract, *Helichrysum arenarium* extract and green coffee oil have the potential to protect against UV radiation with reduced adverse health and environmental effects. However, such natural sunscreens do not shield the full UV light spectrum. In addition, natural phytochemicals are expensive, and large scale manufacturing of such materials has more limitations than synthetic chemical-based sunscreens.

Lignin is a major biopolymer found in plant cell walls. Lignin is an aromatic three-dimensional, amorphous polymer substance. Generally, the lignin structure includes coniferyl alcohol, p-coumaryl alcohol, and sinapyl alcohol moieties. Lignin structures differ based on the source plant, source plant parts, isolation method, and plant environment. Lignin is a sustainable, biodegradable, environmentally benign, and low-cost material. Annually, around 50 million tons of lignin is generated by paper industries. But, 98% of such lignin waste is combusted as fuel, contributing to pollution through greenhouse gas emission. Alternative uses for lignin are therefore desired.

Thus, a lignin-zinc oxide nanohybrid emulsion for UV protection solving the aforementioned problems is desired.

SUMMARY

The lignin-zinc oxide nanohybrid emulsion for UV protection is prepared by mixing lignin with water and dispersing by ultrasonication. The lignin may be derived from *Phoenix dactylifera* (date palm) biomass. In particular, the lignin may be extracted from *Phoenix dactylifera* biomass by a hydrothermal extraction followed by acid precipitation. A zinc salt is then added to the lignin dispersion under stirring, followed by sonication, centrifugation and drying to form a pellet comprising lignin and ZnO nanoparticles bonded thereto, which is referred to as a lignin/ZnO nanohybrid.

A lignin-zinc oxide nanohybrid emulsion is synthesized by mixing the lignin-zinc oxide nanohybrid with water and dispersing by ultrasonication. The dispersed nanohybrid is mixed with oil to form a first mixture. A surfactant is added to the first mixture to form a second mixture, which is then sonicated to form the lignin-zinc oxide nanohybrid emulsion.

The lignin-zinc oxide nanohybrid emulsion effectively blocks transmission of UV radiation, particularly compared to oil or lignin alone. Thus, a method of protecting against UV irradiation may include applying the lignin-zinc oxide nanohybrid emulsion to a surface to be protected.

These and other features of the present disclosure will become readily apparent upon further review of the following specification and drawings.

BRIEF DESCRIPTION OF THE DRAWINGS

FIG. 2 is a composite diffractogram comparing the X-ray Diffraction (XRD) pattern of lignin with the XRD pattern of lignin/ZnO nanohybrids.

FIGS. 3B and 3A are the Energy Dispersive X-Ray Spectroscopy (EDX) spectrum of lignin/ZnO nanohybrids and a SEM micrograph of the corresponding area mapped by the spectrum.

FIGS. 5A and 5B are SEM micrographs of lignin/ZnO nanohybrids.

FIG. 6 is a plot of particle size distribution of lignin/ZnO nanohybrids as shown by Dynamic Light Scattering (DLS).

Similar reference characters denote corresponding features consistently throughout the attached drawings.

DETAILED DESCRIPTION OF THE PREFERRED EMBODIMENTS

Figure 1A:
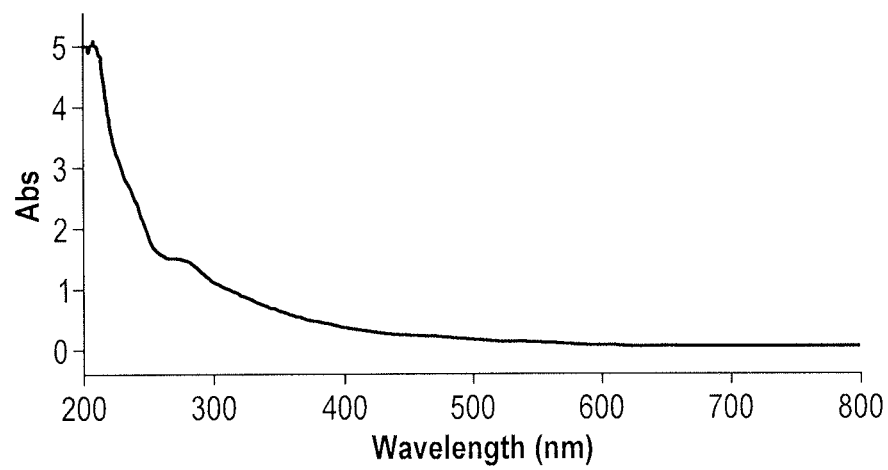
FIG. 1A is the UV-Vis spectrum of lignin/ZnO nanohybrids synthesized as described herein.

The lignin-zinc oxide nanohybrid emulsion for UV protection is prepared by mixing lignin with water and dispersing by ultrasonication. The lignin may be derived from *Phoenix dactylifera* (date palm) biomass. In particular, the lignin may be extracted from *Phoenix dactylifera* biomass by a hydrothermal extraction followed by acid precipitation. A zinc salt is then added to the lignin dispersion under stirring, followed by sonication, centrifugation and drying to form a pellet comprising lignin and ZnO nanoparticles bonded thereto, which is referred to as a lignin/ZnO nanohybrid. The zinc salt may be zinc acetate.

A lignin-zinc oxide nanohybrid emulsion is synthesized by mixing the lignin nanohybrids with water and dispersing the lignin nanohybrids by ultrasonication to form a dispersed lignin nanohybrid solution. The dispersed lignin nanohybrid solution is mixed with oil to form a first mixture. A surfactant is added to the first mixture to form a second mixture, which is then sonicated to form the lignin-zinc oxide nanohybrid emulsion. The emulsion forms droplets that are nanometer-sized, and is therefore a nanoemulsion.

Both the lignin-zinc oxide nanohybrids and the lignin-zinc oxide nanohybrid emulsion effectively block transmission of UV irradiation, particularly when compared to oil or lignin alone. Thus, a method of protecting against UV irradiation may include applying the lignin-zinc oxide nanohybrids or the lignin-zinc oxide nanohybrid emulsion to a surface to be protected. The surface to be protected may be an organism's skin.

Generally, plant biomass includes hemicellulose, lignin, and cellulose, among other components. However, the composition of plant biomass varies from one plant to another plant. The date tree biomass has a high concentration of cellulose (39-47%) and lignin (32-35%) and a lower concentration of hemicellulose (15-25%). Interestingly, a date palm leaflet includes 41-43% cellulose and 32-36% lignin. Moreover, a date palm leaf stalk includes 44-47% cellulose and 33-38% lignin. Compared with other parts of date palm, the leaflet and leaf stalk-based waste generation is very high and has high cellulose and lignin content. Thus, date palm biomass is highly suitable for synthesis of cellulose, lignin, and carbon-based nanostructures.

It should be understood that the amounts of materials used to illustrate the methods described herein are exemplary, and appropriate scaling of the amounts is encompassed by the present subject matter, so long as the relative ratios of materials are maintained. As used herein, the term "about," when used to modify a numerical value, means within ten percent of that numerical value. As used herein, the prefix "nano", in the context of particles or emulsions, refers to a characteristic size of the particles or emulsions being within the range of 1-999 nm.

The following examples illustrate the present disclosure.

Example 1

Synthesis of Lignin-Zinc Oxide Nanohybrids and Lignin-Zinc Oxide Nanohybrid Emulsion A sample of *Phoenix dactylifera* biomass (composed primarily of leaves, i.e., leaflet, rachis, stalk, petiole, and spines) was collected from the King Saud University Campus, Riyadh (Saudi Arabia). The collected biomass was dried in a dark, room temperature environment, cut into small pieces, and pulverized in a blender to produce a biomass powder. About 25 g of biomass powder was immersed in 4% of 1 L sodium hydroxide alkali aqueous solution (40 g sodium hydroxide in 1 L water), and the biomass in solution was autoclaved at 120° C. for 2 hours under 15 lb of pressure, resulting in a black liquor with solids. The black liquor was separated by filtration through Whatman filter paper. The black liquor was pH adjusted to a pH of 2.0 using hydrochloric acid and kept at room temperature until a black precipitate formed in the pH-adjusted black liquor. The black precipitate was isolated by centrifugation. The isolated black precipitate was dried at room temperature to produce isolated lignin.

Then, 100 mg of the isolated lignin was mixed with 50 mL of distilled water and dispersed using ultrasonication. About 50 mL of 0.001 M zinc acetate solution (in water) was added to the dispersed lignin solution under stirring to form a zinc/lignin mixture. The zinc/lignin mixture was sonicated for 45 minutes using probe sonication at 750 W. Subsequently, the mixture was centrifuged at 20,000 rpm for 15 minutes. The resulting pellet was isolated by removing supernatant and dried at room temperature. The resulting dried pellet comprises the exemplary lignin-zinc oxide nanohybrids.

Either 50 mg of isolated lignin (as control) or the exemplary lignin-zinc oxide nanohybrids were mixed with 25 mL of distilled water and dispersed using ultrasonication. The sonicated lignin or the lignin-zinc oxide nanohybrid solution was mixed with an oil to form a first mixture at a ratio of 100 mL sonicated lignin or lignin-zinc oxide nanohybrid solution to 5 mL oil. Various oils were used in exemplary synthesis methods of the present disclosure, the oils being chosen from coconut oil, castor oil, sunflower oil, sesame oil, olive oil, and corn oil. In particular, in the following Examples 2-3 showing characterization studies and UV protection, coconut oil was used. It should be understood that an oil other than those listed may be selected to best suit the ultimate desired application. A surfactant was added to the first mixture to form a second mixture. The surfactant was chosen from either Tween 20 or Tween 80 (Tweens are polyethylene or polyoxyethylene sorbitol ester derivatives, either laureates [Tween 20] or oleates [Tween 80]) in the exemplary synthesis methods performed, but it should be understood that a surfactant other than those mentioned may be selected to stabilize the oil-water emulsion. Subsequently, the second mixture was sonicated for 30 minutes at 750 W using a probe sonicator, producing a lignin emulsion used as a control or the lignin-zinc oxide nanohybrid emulsion (or nanoemulsion), which appeared as a light brown colloidal formulation for which UV shielding behavior was assessed, as in the following additional examples.

Example 2

Characterization of Lignin Nanohybrids and Lignin Nanohybrid Nanoemulsion

The morphology and chemical composition of the lignin emulsion and the lignin-zinc oxide nanohybrid emulsion were analyzed using Field Emission Scanning Electron Microscopy (FE-SEM) and Energy-Dispersive X-ray Spectroscopy (EDX) respectively. The formulation droplet size and stability was assessed using Dynamic Light Scattering (DLS) analysis.

Figure 1B:
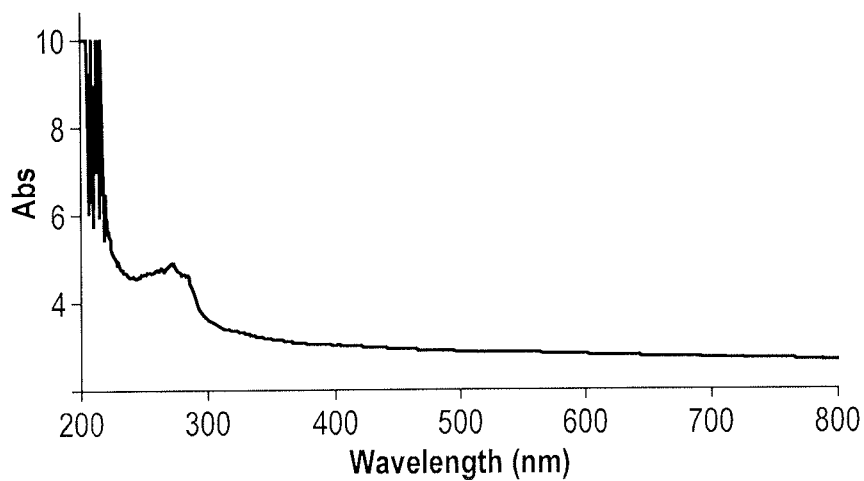
FIG. 1B is the UV-Vis spectrum of a lignin/ZnO nanohybrid emulsion synthesized as described herein.
Figure 4A:
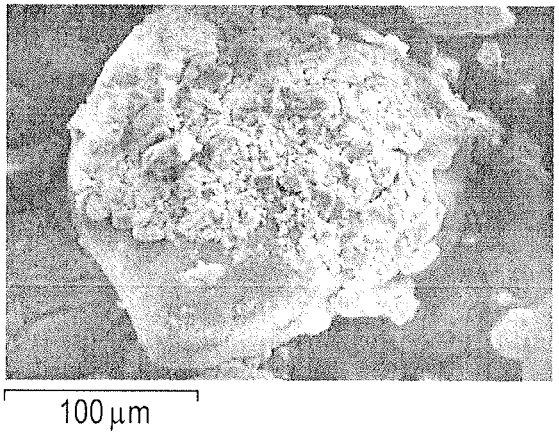
FIGS. 4A, 4B, 4C, and 4D are EDX elemental mapping micrographs of C, O and Zn in lignin/ZnO nanohybrids synthesized as described herein.
Figure 4B:
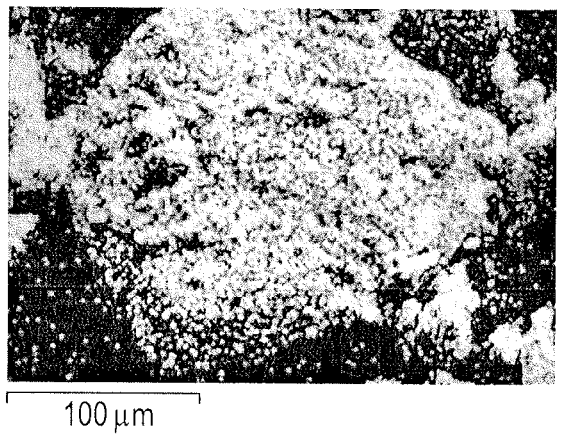
Figure 4C:
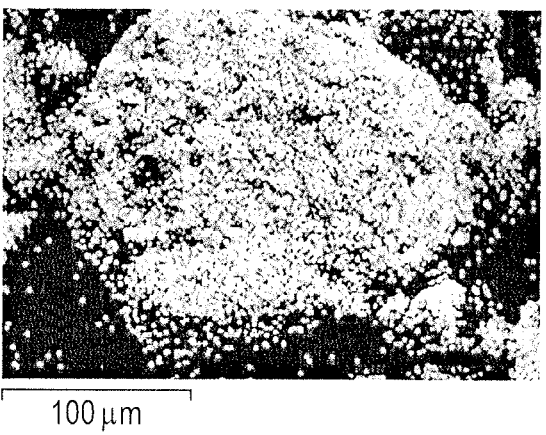
Figure 4D:
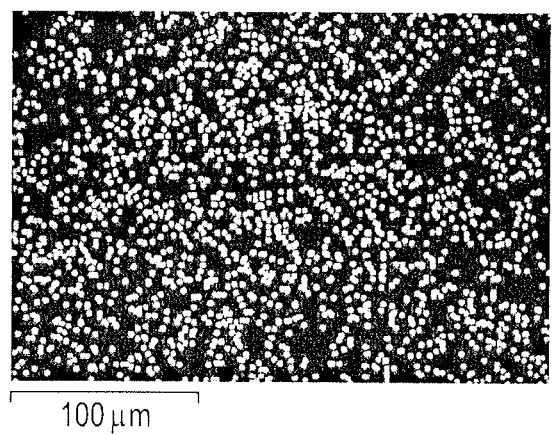

UV spectra of the exemplary lignin-zinc oxide nanohybrids and the exemplary lignin-zinc oxide nanohybrid emulsion are shown in FIGS. 1A-1B. The lignin nanohybrids showed a peak at 275 nm, presumably due to intrinsic isolated lignin architecture (FIG. 1A). Also, the exemplary lignin-zinc oxide nanohybrid emulsion showed a broader peak between 290-300 nm.

The crystalline nature of the exemplary extracted lignin and exemplary lignin nanohybrids was assessed by XRD, as shown in FIG. 2. The lignin-zinc oxide nanohybrid data (dark grey) shows several sharp peaks at 2θ values of 31.6°, 34.4°, 36.2°, 47.3°, 56.4°, 62.7° and 68.9°, which correspond to ZnO lattice planes (100), (002), (101), (102), (110), (103), (112) and (201), respectively. A broad peak between 10°-20° appearing in the lignin alone (light grey) and lignin-zinc oxide nanohybrids is attributed to lignin polymer.

The elemental composition of the lignin-zinc oxide nanohybrids is further illustrated and confirmed in FIGS. 3A-3B. The results of EDX analysis of the exemplary lignin-zinc oxide nanohybrids clearly indicate the presence of C, O and Zn, consistent with the makeup of lignin and ZnO. No other elements indicative of impurities were observed. FIGS. 3A-3B show the EDX mapping of the elements dispersion. These results show that the ZnO appears distributed throughout the lignin evenly. Table 1 shows the relative abundance of C, O and Zn according to the EDX analysis, showing that the lignin nanohybrids contain 5.95% Zn by weight percentage. Thus, the lignin-zinc oxide nanohybrids are made of a relative large quantity of lignin and a small quantity of ZnO.

TABLE 1

Chemical Composition of Lignin-Zinc Oxide Nanohybrids

| Element | Weight % | Atomic % |
|---|---|---|
| C K | 48.51 | 57.89 |
| O K | 45.54 | 40.80 |
| Zn L | 5.95 | 1.30 |

The structure and morphology of the exemplary lignin-zinc oxide nanohybrids were investigated using field emission scanning electron microscopy (FE-SEM). FIGS. 5A-5D depict FE-SEM micrographs of the exemplary lignin-zinc oxide nanohybrids. These results indicate 50-100 nm size ZnO nanostructures are attached to a lignin matrix. Under ultrasonication, lignin presumably reduces and stabilizes the ZnO nanoparticles due to their free aliphatic hydroxyl and phenolic hydroxyl groups. The particle size distribution determined by DSL is shown in FIG. 6. The result shows the lignin-zinc oxide nanohybrids' average particle size is 172 nm. The physicochemical analyses cummulatively confirm lignin/ZnO nanohybrid formation.

Example 3

UV Blocking Activity of Lignin Emulsion and Lignin-Zinc Oxide Nanohybrid Emulsion Furthermore, the exemplary lignin-zinc oxide nanohybrids were used as a platform for a UV-blocking formulation by incorporation into an oil emulsion, as discussed previously. In the following examples, the oil used was coconut oil. Exemplary lignin-zinc oxide nanohybrid emulsion, exemplary lignin emulsion, coconut oil and isolated lignin were each prepared and their respective UV blocking activities were tested as follows (FIGS. 7-8).

Lignin-zinc oxide nanohybrid emulsion, lignin emulsion, oil alone or isolated lignin alone was applied to 3M Transpore Tape adhered to a clean quartz plate; for each measurement, one of lignin-zinc oxide nanohybrid emulsion, lignin emulsion, coconut oil and isolated lignin were spread over the entire surface of the 3M Transpore Tape, which was adhered to the clean quartz plate slowly with a thimble-coated finger. The sample-coated tape was then dried in a dark room for 30 min. UV transmittance was measured using a UV spectrophotometer equipped with a solid sample holder (Agilent Technologies, USA).

Figure 7:
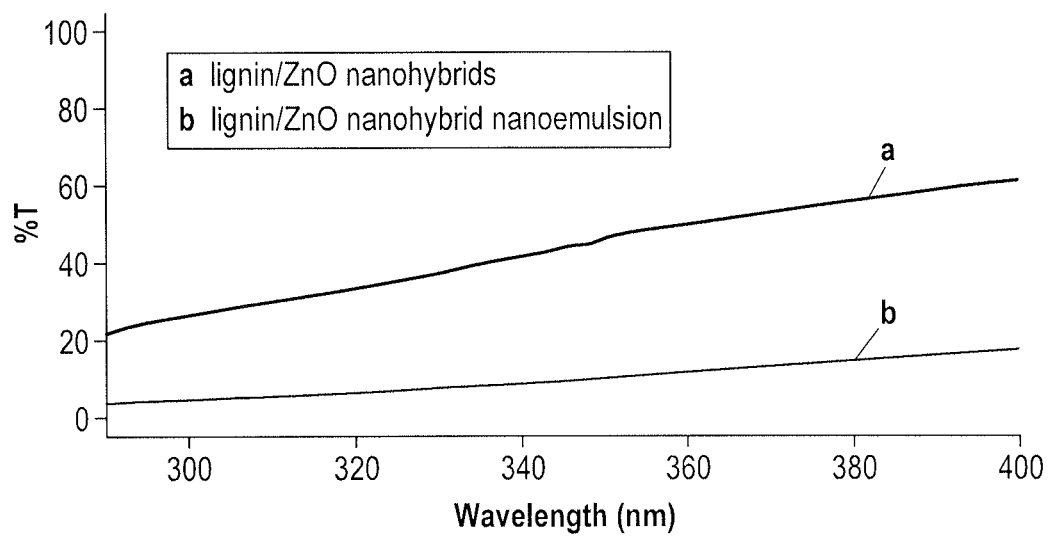
FIG. 7 is a comparison of UV shielding of lignin/ZnO nanohybrids and lignin/ZnO nanohybrid emulsion synthesized as described herein as shown by a plot of percent transmittance as a function of wavelength.
Figure 8:
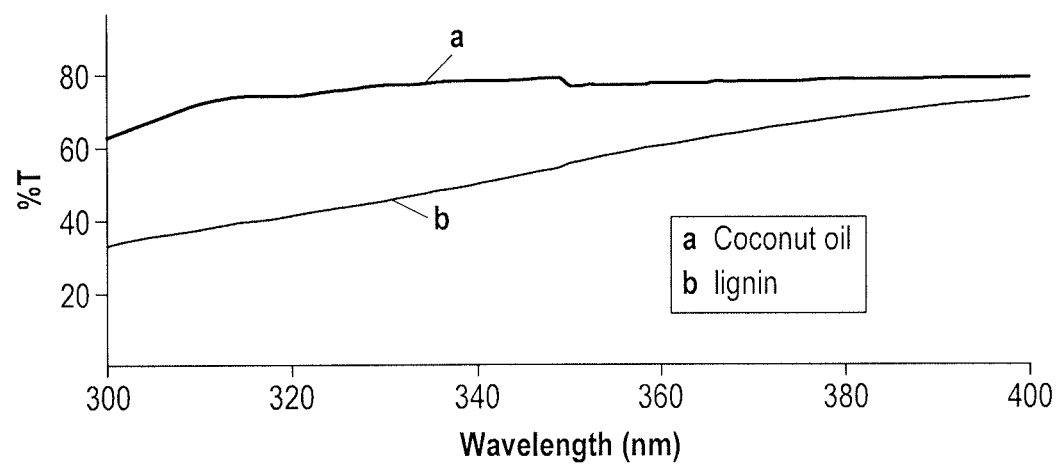
FIG. 8 is a comparison of UV shielding of coconut oil alone and lignin alone as shown by a plot of percent transmittance as a function of wavelength.

The lignin-zinc oxide nanohybrids absorbed around 80% of UV radiation, whereas the lignin-zinc oxide nanohybrid emulsion absorbed more than 95% of UV radiation (FIG. 7). Moreover, the lignin-zinc oxide nanohybrid emulsion absorbed in UVA and UVB wavelengths. In contrast, coconut oil and lignin alone absorbed around 40% and 65% of UV radiation, respectively. Clearly the lignin-zinc oxide nanohybrid emulsion effectively blocks a broad spectrum of UV radiation.

The lignin-zinc oxide nanohybrid emulsion is derived from naturally available materials and is, thus, non-toxic, green, and biocompatible, in addition to effectively blocking a broad spectrum of UV radiation. The results indicate that the lignin-zinc oxide nanohybrid emulsion may be suitable for sunscreens or other UV protection.

It is to be understood that the lignin-zinc oxide nanohybrid emulsion for UV protection is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of synthesizing a lignin-zinc oxide nanohybrid emulsion for UV protection, comprising the steps of:
   sonicating lignin in distilled water to obtain an aqueous lignin dispersion;
   adding zinc acetate to the lignin dispersion with stirring to obtain a mixture;
   sonicating the mixture for forty-five minutes using probe sonication to obtain an aqueous dispersion of lignin-zinc oxide nanohybrids;
   adding a biocompatible oil and a surfactant to the aqueous dispersion of lignin-zinc oxide nanohybrids to obtain a second mixture; and
   sonicating the second mixture for thirty minutes using probe sonication to obtain the lignin-zinc oxide nanohybrid emulsion.

2. The method of synthesizing a lignin-zinc oxide nanohybrid emulsion according to claim 1, wherein the lignin-zinc oxide nanohybrid emulsion comprises a nanoemulsion.

3. The method of synthesizing a lignin-zinc oxide nanohybrid emulsion according to claim 1, further comprising the step of extracting the lignin from Phoenix dactylifera.

4. The method of synthesizing a lignin-zinc oxide nanohybrid emulsion according to claim 3, wherein the step of extracting the lignin from Phoenix dactylifera comprises the steps of:
   pulverizing dried leaves of Phoenix dactylifera in a blender to obtain a biomass powder;
   immersing the biomass powder in an aqueous solution of sodium hydroxide;
   heating the aqueous solution of sodium hydroxide containing the biomass powder at 120° C. under 15 lbs. of pressure to obtain a black liquor;
   filtering the black liquor to obtain a filtrate;
   adding hydrochloric acid to the filtrate to adjust the pH of the black liquor to 2.0; and
   centrifuging the acidified black liquor to obtain the lignin as a precipitate.

5. The method of synthesizing a lignin-zinc oxide nanohybrid emulsion according to claim 4, wherein the leaves of Phoenix dactylifera comprise leaves of date palms grown in Saudi Arabia.

6. The method of synthesizing a lignin-zinc oxide nanohybrid emulsion according to claim 1, wherein the step of adding a biocompatible oil comprises adding an oil selected from the group consisting of coconut oil, castor oil, sunflower oil, sesame oil, olive oil, and corn oil.

7. The method of synthesizing a lignin-zinc oxide nanohybrid emulsion according to claim 1, wherein the step of adding a biocompatible oil comprises adding coconut oil to the aqueous dispersion of lignin-zinc oxide nanohybrids.

8. The method of synthesizing a lignin-zinc oxide nanohybrid emulsion according to claim 1, wherein the step of adding a biocompatible oil and a surfactant comprises adding a surfactant selected from the group consisting of polyethylene glycol sorbitan monolaurate and polyethylene glycol sorbitan monooleate to the aqueous dispersion of lignin-zinc oxide nanohybrids.

\* \* \* \* \*